United States Patent
Sokolov et al.

(10) Patent No.: US 7,656,524 B2
(45) Date of Patent: Feb. 2, 2010

(54) HIGH CONTRAST TIP-ENHANCED RAMAN SPECTROSCOPY

(75) Inventors: Alexei P. Sokolov, Copley, OH (US); Alexander Kisliuk, Akron, OH (US); Disha Mehtani, Akron, OH (US); Ryan D. Hartschuh, Copley, OH (US); Nam-Heui Lee, Seongnam-Si (KR)

(73) Assignee: The University of Akron, Akron, OH (US)

( * ) Notice: Subject to any disclaimer, the term of this patent is extended or adjusted under 35 U.S.C. 154(b) by 14 days.

(21) Appl. No.: 11/815,984

(22) PCT Filed: Feb. 15, 2006

(86) PCT No.: PCT/US2006/005429

§ 371 (c)(1), (2), (4) Date: Mar. 26, 2008

(87) PCT Pub. No.: WO2006/089000

PCT Pub. Date: Aug. 24, 2006

(65) Prior Publication Data

US 2008/0266557 A1    Oct. 30, 2008

Related U.S. Application Data

(60) Provisional application No. 60/653,024, filed on Feb. 15, 2005.

(51) Int. Cl.
*G01J 3/44* (2006.01)
*G01N 21/65* (2006.01)

(52) U.S. Cl. .................................... 356/301
(58) Field of Classification Search .............. 356/301
See application file for complete search history.

(56) References Cited

U.S. PATENT DOCUMENTS

| 6,643,012 B2* | 11/2003 | Shen et al. ............... 356/301 |
| 2002/0105641 A1 | 8/2002 | Anderson |
| 2004/0174521 A1* | 9/2004 | Drachev et al. ............ 356/301 |

FOREIGN PATENT DOCUMENTS

WO    WO 2004/090505 A2    10/2004

OTHER PUBLICATIONS

Wessel, J., Surface-enhanced optical microscopy, J. Opt. Soc. Am. B 1985, 2, No. 9, pp. 1538-1540.
Sun, Z.X. et al, Apertureless near-field scanning Raman microscopy using reflection scattering geometry, Ultramicroscopy 94 2003, pp. 237-244.
Novetny, L. et al, Theory of Nanometric Optical Tweezers, Physical Review Letters 1997, 79, No. 4, pp. 645-648.

(Continued)

*Primary Examiner*—F. L Evans
(74) *Attorney, Agent, or Firm*—Roetzel & Andress; Joseph J. Crimaldi (57) ABSTRACT

The present invention relates generally to the field of spectroscopy, and more particularly to tip-enhanced Raman spectroscopy that provides an enhanced contrast-ratio of a near-field Raman signal to a background signal. The near-field Raman signal is captured from a small volume of material near a metal-coated tip thereby achieving submicron lateral resolution.

12 Claims, 8 Drawing Sheets

OTHER PUBLICATIONS

Gersten, J. et al, Spectroscopic properties of molecules interacting with smal dielectric particles, J. Chem. Phys. 1981, 75(3), pp. 1139-1152.

Pettinger, B. et al, Nanoscale Probing of Adsorbed Species by Tip-Enhance Raman Spectroscopy, Physical Review Letters 2004, 92, No. 9, pp. 096101-1 - 096101-4.

Martin, O.J. et al, Controlling and tuning strong optical field gradients at a local probe microscope tip apex, Appl. Phys. Lett. 1997, 70(6), pp. 705-707.

Hayazawa, N. et al, Near-field enhanced Raman spectroscopy using side illumination optics, Journal of Applied Physics 2002, 92, No. 12, pp. 6983-6986.

Anderson, M.S. et al, A Raman-atomic force microscope for apertureless-near-field spectroscopy and optical . . . , Review of Scientific Instruments 2002, 73, No. 3, pp. 1198-1203.

Anderson, M.S., Locally enhanced Raman Spectroscopy with an atomic force microscope, Applied Physics Letters 2000, 76, No. 21, pp. 3130-3132.

Tada, T. et al, Fabrication of Photinic Crystals Using Metal Clusters as Nuclei for Self-formation of Etching Masks, MRS Sym Proc. 2004, 636.

* cited by examiner

HIGH CONTRAST TIP-ENHANCED RAMAN SPECTROSCOPY

FIELD OF THE INVENTION

The present invention relates generally to the field of spectroscopy, and more particularly to tip-enhanced Raman spectroscopy that provides an enhanced contrast-ratio of a near-field Raman signal to a background signal. The near-field Raman signal is captured from a small volume of material near a metal-coated tip, thereby achieving submicron lateral resolution.

BACKGROUND OF THE INVENTION

The general concept of Raman signal enhancement near a sub-micrometer-sized metal particle disposed at a tip has been proposed and realized. The presence of a metal particle at the tip enhances the strength of an electrical field of light, thereby inducing enhancement of that portion of the total Raman signal within 10 to 20 nm of the particle's surface. This portion of the total Raman signal adjacent to the surface of the metal particle is referred to herein as the near-field signal and the portion of the total Raman signal outside this region is the far-field signal. In this way, the spatial resolution of Raman spectroscopy can be improved, in one embodiment, to approximately the radius of the tip provided with the metal particle (approximately 10 nm in one instance). This is far below the traditional diffraction limit of light, which is about 500 nm. This idea has recently been embodied in the form of tip enhanced Raman spectroscopy (TERS), which couples a Raman spectrometer to an atomic force microscope (AFM) with a metallic or metal-coated tip.

A TERS signal has two main components: one coming from the near vicinity of the tip (the near-field signal), and another coming from the rest of the laser illuminated area, this other component being referred to herein as the far-field signal. To obtain effective results from TERS, the contrast ratio of the near-field signal strength to the far-field signal strength must be high—i.e., the near-field signal should be much stronger than the far field signal. Raman mapping (analysis of chemical structure, composition, stresses, etc.) with extreme lateral resolution can be achieved if the contrast ratio is high without further data manipulation. Known reported TERS measurements on silicon (Si) exhibit an approximate 30-50% increase in the total TERS signal over the far-field Raman signal alone, resulting in a contrast ratio of near-field to far-field signal about 0.3 to 0.5. This small contrast is insufficient for scanning TERS and will require subtraction of the far-field signal to achieve useful results. Such corrections will introduce significant uncertainty, strongly decrease the accuracy of the measurements, and drastically increase measurement time. The higher the contrast the better, but for practical purposes, a contrast ratio of at least about 3, or even higher, is desirable.

Variations on the TERS technique include bottom, top, and side illumination geometries, where the light source is positioned in the respective orientations relative to the sample to be mapped using TERS. The use of top-illumination geometry with a depolarization configuration has been proposed to increase TERS contrast for mapping Si. Since Raman-scattered light from Si is strongly polarized (there is no change in polarization of the illumination light upon being scattered), the far-field Raman signal can be suppressed by using a depolarizing optical configuration, i.e., by measuring the scattered light spectra with polarization perpendicular to the polarization of the illumination beam. In such a case, the metal particles at the tip depolarize the illumination light and induce depolarized scattering of Si in the vicinity of the particle. Therefore, the total depolarized TERS signal is mainly due to the near-field contribution and the far-field signal is strongly suppressed. The resulting contrast between the depolarized TERS and the normal Raman signal is greater than that from TERS without a depolarization configuration. However, the proposed top-illumination geometry poses several problems to commercialization. First, the tip (an Ag particle at the end of a quartz tip) and the sample are submerged in glycerol to eliminate scattering and shadowing from the quartz tip. It is neither simple nor convenient to work in this configuration. Second, the silver particle, which has an approximately 50 to 100 nm radius, lies between the Si and the signal collecting optics. This geometry has a number of disadvantages: (i) it restricts the near-field Raman signal to the edges of the particle; (ii) it limits lateral resolution to at least the size of the particle or even larger (approximately 100 nm); (iii) the maximum enhanced signal from the Si surface closest to the particle is lost (shadowed by the particle).

Accordingly, there is a need in the art for a TERS method and system that can achieve a high contrast ratio of at least 3, with improved lateral resolution (in one embodiment, about 10 to about 30 nanometers). The system should be able to map both transparent and non-transparent materials, and should minimize the complexity of performing TERS mapping.

SUMMARY OF THE INVENTION

The present invention relates generally to the field of spectroscopy, and more particularly to tip-enhanced Raman spectroscopy that provides an enhanced contrast-ratio of a near-field Raman signal to a background signal. The near-field Raman signal is captured from a small volume of material near a metal-coated tip, thereby achieving submicron lateral resolution.

In one embodiment, the present invention relates to a method for conducting Raman spectroscopy, the method comprising the steps of: (a) using an illumination/collection optics objective to illuminate one or more samples with light, wherein the illumination/collection optics objective is oriented at an angle of about 10° to about 90° relative to the longitudinal axis of a tip; (b) using an illumination polarization means to polarize at least a portion of the light of step (a) thereby generating a polarization orientation in at least a portion of the light of step (a), wherein the polarization orientation is from about 50° to about 80° relative to the longitudinal axis of the tip; (c) using a scattered polarization analyzer to selectively transmit at least a portion of the polarized light from step (b), wherein the polarization of the light transmitted by the scattered polarization analyzer is oriented at an angle of about 0° to about 90° relative to the longitudinal axis of the tip so as to maximize the tip-enhanced Raman contrast and wherein the orientation angle of the scattered polarization analyzer is selected based on the nature of the one or more samples being analyzed; and (d) collecting spectral data generated in steps (a) through (c) via a suitable collection means for analysis.

In another embodiment, the present invention relates to an instrument for conducting Raman spectroscopy comprising: (a) an illumination/collection optics objective lens designed to illuminate one or more samples with light, wherein the illumination/collection optics objective lens is oriented at an angle of about 10° to about 90° relative to the longitudinal axis of a tip; (b) an illumination polarization means designed to polarize at least a portion of the light of step (a) thereby generating a polarization orientation in at least a portion of the light of step (a), wherein the polarization orientation is from about 50° to about 80° relative to the longitudinal axis of the tip; (c) a scattered polarization analyzer designed to selectively transmit at least a portion of the polarized light from step (b), wherein the polarization of the light transmitted by the scattered polarization analyzer is oriented at an angle of about 0° to about 90° relative to the longitudinal axis of the tip so as to maximize the tip-enhanced Raman contrast and wherein the orientation angle of the scattered polarization analyzer is selected based on the nature of the one or more samples being analyzed; and (d) a data collection means designed to collect spectral data generated in steps (a) through (c) for analysis.

BRIEF DESCRIPTION OF THE DRAWINGS

FIG. 6a is a cross-sectional illustration of an Si/SiO$_x$ structure;

FIG. 6b is an illustration of line scans comparing the integrated Raman intensity of the near-field signal and the far-field signal with the topography of the structure of FIG. 6a;

FIG. 6c illustrates the correlation between the inverted topography line scan (solid line) and integrated Raman intensity line scan (▲);

FIG. 7a is a two-dimensional topographical image of an Si/SiO$_x$ structure formed in accordance with the design illustrated in FIG. 6a;

FIG. 7b is a TERS image of an Si/SiO$_x$ structure formed in accordance with the design illustrated in FIG. 6a;

DESCRIPTION OF THE INVENTION

The present invention relates generally to the field of spectroscopy, and more particularly to tip-enhanced Raman spectroscopy that provides an enhanced contrast-ratio of a near-field Raman signal to a background signal. The near-field Raman signal is captured from a small volume of material near a metal-coated tip thereby achieving submicron lateral resolution.

Certain terminology is used herein for convenience only and is not to be taken as a limitation on the present invention.

The contrast ratio is the ratio of the near-filed signal (total signal minus the far-field signal) to the far-field signal and can be represented mathematically as: $C=I_{near}/I_{far} \approx (I_{total}-I_{far})/I_{far}=I_{total}/(I_{far}-1)$, where I is the signal intensity. To achieve the desired contrast ratio, the enhancement factor of the tip is to be maximized, the far-field intensity is to be minimized, or a combination of both. The enhancement factor refers to the increase in near-field Raman signal due to metal particle plasmon resonance. The enhancement factor is estimated as the ratio of the signal in the vicinity of the tip to the signal without the tip, both signals being calculated per unit volume, i.e., it is the ratio $I_{near}/V_{near}$ to $I_{far}/V_{far}$, where V is the volume contributing to the signal.

The enhancement factor represents a scalar multiple by which the near-field intensity is to be increased to obtain a suitable contrast ratio, and not the increase in total signal intensity. Previously known TERS enhancement factors have been reported to be on the order of $10^4$. The volume of the near-field can be estimated as a semi-sphere with a radius of about 20 nanometers, and thus, $V_{near}$ is about $2 \times 10^{-5}$ $\mu m^3$. Similarly, $V_{far}$ is estimated as the cross-sectional area of a spot size (approximately 1 to 2 $\mu m^2$) of a laser used to illuminate the specimen multiplied by whatever is the smallest: the sample thickness, light penetration depth (approximately 0.5 $\mu m$ for Si at the laser wavelength 514 nm), or the focal depth of the confocal optics used (approximately 1 $\mu m$). So, $V_{far}$ can be estimated as about 0.5 $\mu m^3$, for experimental purposes, on Si. Assuming an enhancement factor of about $10^4$ in this case, a contrast of about 40% is expected for Si. This contrast is not sufficient. For practical purposes it should be at least about 300% or higher. In another embodiment, the contrast yielded by the present invention is at least about 300% to about 800% higher, or from about 350% to about 700% higher, or even from about 400% to about 600% higher. In still another embodiment, the contrast yielded by the present invention is at least about 3 or more, when not expressed as a percent. In still another embodiment, the contrast yielded by the present invention is at least about 3 to about 8, or from about 3.5 to about 7 or even from about 4 to about 6, when not expressed as a percent.

To achieve a suitable contrast ratio, the present invention seeks to suppress or minimize the effect of the far-field signal, thereby yielding an increase in the contrast ratio. In one embodiment, the present invention comprises an illumination polarization and collection polarization combination that has axes oriented at angles relative to the longitudinal axis of the tip. The orientation of the angles maximizes the contrast ratio of TERS via effective suppression of the far-field signal without significantly attenuating the near-field intensity.

A side-illumination geometry is implemented along with a specific polarization arrangement. A light source is to be arranged in a side-illumination position and targeted toward the specimen. It is believed, and supported by simulations, that the illumination angle at which maximum enhancement occurs changes with tip geometry, but maximum enhancement is expected at an angle near 35° to 40°. However, the present invention includes directing illumination light onto a specimen at an illumination angle. In one embodiment, the illumination angle can be between about 0° and about 90° relative to a longitudinal axis of a tip. In another embodiment, the illumination angle can be between about 45° and about 85°, or even about 50° and about 80° relative to a longitudinal axis of a tip.

As previously mentioned, Raman-scattered light from Si is strongly polarized. In a top illumination scheme, by measuring depolarized scattering, the normal far-field Raman signal of Si is suppressed since polarized scattered light is blocked by an analyzer in the collection optics. The metal-coated tip will depolarize illumination and scattered light and thereby enhance detection of the near-field signal since depolarized light will pass through the analyzer. This creates a high contrast between the far-field and near-field signals. In a side illumination scheme, maximum contrast can be achieved by selecting a specific combination of illumination and scattered polarizations.

For side illumination TERS, the enhancement factor is dependent at least partially on illumination light polarization. P-polarized light (polarized parallel to tip axis) is enhanced to a greater degree relative to s-polarized light (polarized perpendicular to tip axis) illumination light. Light polarized parallel to the longitudinal axis of a long sub-micrometer sized metal particle (or tip) creates greater enhancement from the metal.

Accordingly, in one embodiment of the present invention a polarizer is provided for polarizing illumination light at an angle of about 50 to about 70° relative to the tip axis and an additional use of analyzer with an orientation relative to the polarization axis of the polarizer that maximizes the contrast ratio for side-illumination geometry. The angle of illumination light polarization chosen will satisfy two criteria: (1) the angle will maximize enhancement of the near-field signal; and (2) the near-field signal will not be suppressed by the analyzer that suppresses the far field signal. Use of s-polarization does not satisfy the first criteria. While not wishing to be bound to any one theory, it is believed that the best enhancement is achieved with p-polarization, which is referred to herein as conventional polarization. However, the signal with p-polarization will be suppressed by an analyzer that transmits depolarized light only. Thus, this configuration does not satisfy the second criteria and the angle should be chosen there between.

Embodiments of the present invention can have any analyzer angle for Si that falls within the range of about 40° to about 90°, relative to the tip axis. Here, and elsewhere in the specification, such angle ranges include all incremental angles and partial angles therein, and are not to be limited to solely to the external ranges stated above.

Through the use of an analyzer angle for Si that falls within the range of about 40° to about 90°, the present invention provides, unexpectedly, suitable contrast ratios, which had traditionally been thought to arise from a perfectly perpendicular, or de-polarized, orientation. The orientation of the analyzer also depends on the material, orientation of polarization relative to the crystallographic axis of the material and on the polarization properties of the Raman mode analyzed. In the case of silicon, for example, an analyzer angle that provides a suitable contrast ratio appears to be comparable to the angle of the illumination polarization. Thus, for a 70° angle of polarization, the primary axis of the analyzer is also oriented at approximately 70°±10°. For CdS, however, the analyzer angle differs from the illumination polarization by about 20° to about 60° and is oriented at an angle of about 15° to about 35° relative to the longitudinal axis of the tip.

Figure 1:
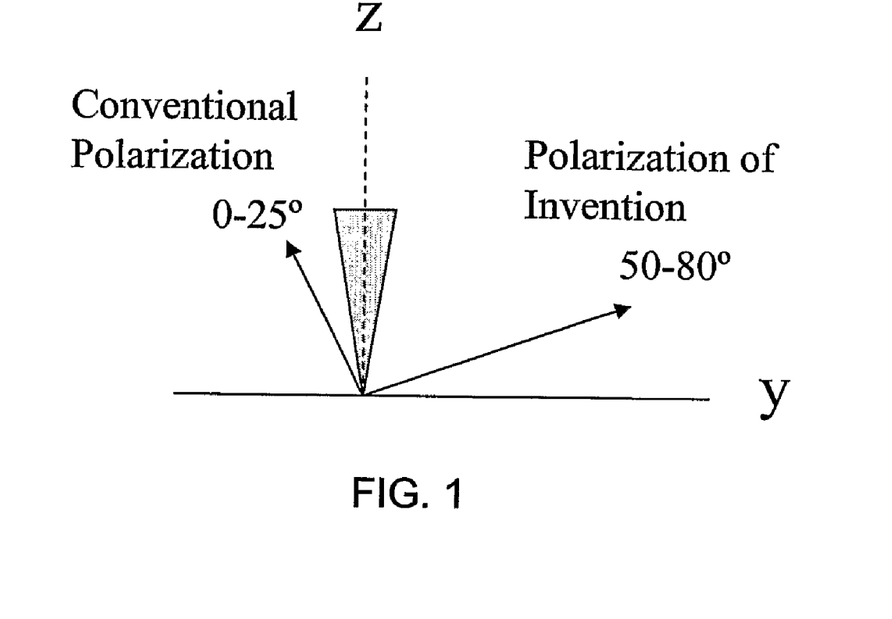
FIG. 1 is a schematic illustration of a metallic tip in contact with a specimen, in the ZY-plane, illumination polarizations for conventional and optimum angles for side illumination are indicated.

Turning to the Figures, FIG. 1 is a schematic illustration showing a tip (the shaded portion) in contact with a sample, conventional illumination polarization near parallel to the tip axis (0° to 25°), and illumination polarization of the present invention 50° to 80° from the tip axis. The analyzed light polarization for the case of Si is within 0° to 10° of the illumination polarization. The best angles for the analyzed polarization depends on the material being analyzed. FIG. 1 is shown in the direction of beam propagation.

Figure 2:
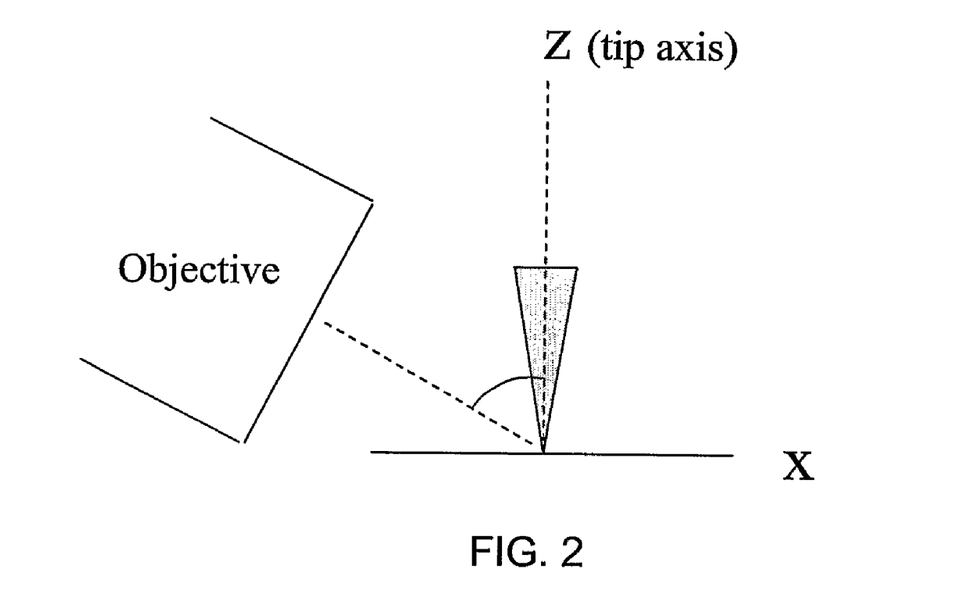
FIG. 2 is a schematic illustration of a metallic tip in contact with a specimen in the ZX-plane illustrating the orientation of an illumination/collection optics objective lens arranged within the range of 0° to 90° relative to the tip axis, or so called side illumination.

FIG. 2 is a schematic illustration showing a tip (the shaded portion) in contact with a sample and the illumination angle of objective relative to the tip axis.

FIG. 2 is a side view of the beam propagation.

Figure 3:
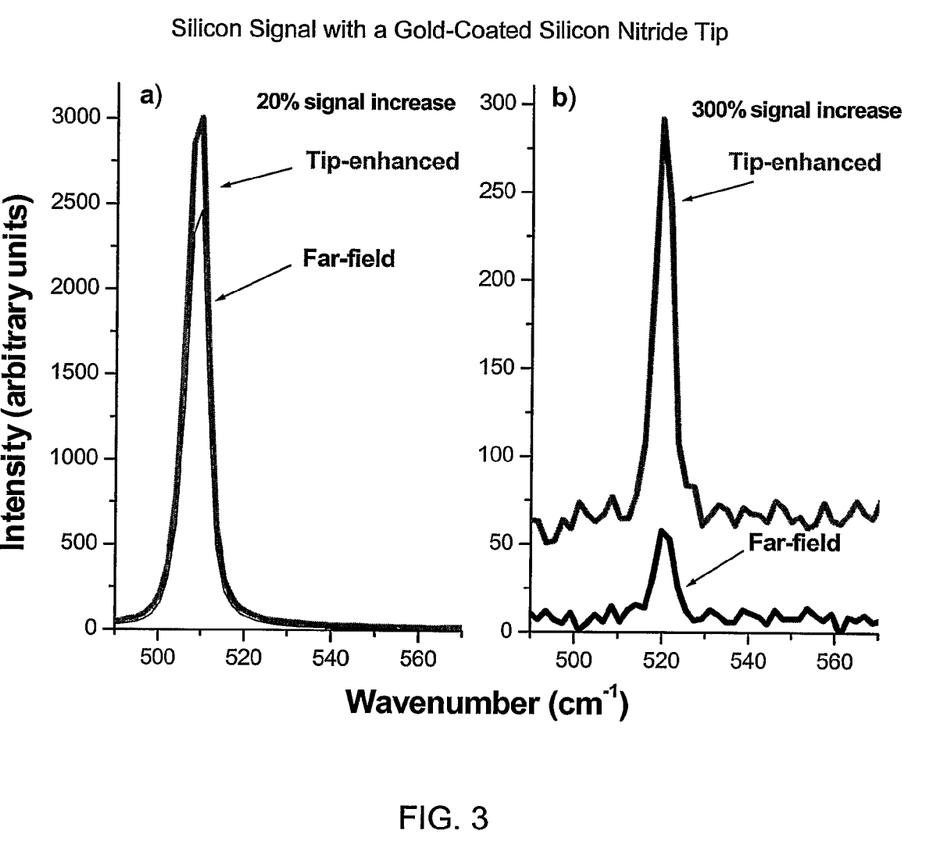
FIG. 3 provides a comparison of the tip-enhanced Raman results obtained for Si using conventional means (a) with those obtained according to the present invention (b)

FIG. 3 are two graphs illustrating an increase of a TERS signal from Si in FIG. 3a (conventional polarization conditions) and FIG. 3b (polarization conditions of the present invention). An increase in contrast of approximately 10 times can be achieved with one embodiment of the present invention.

Figure 4:
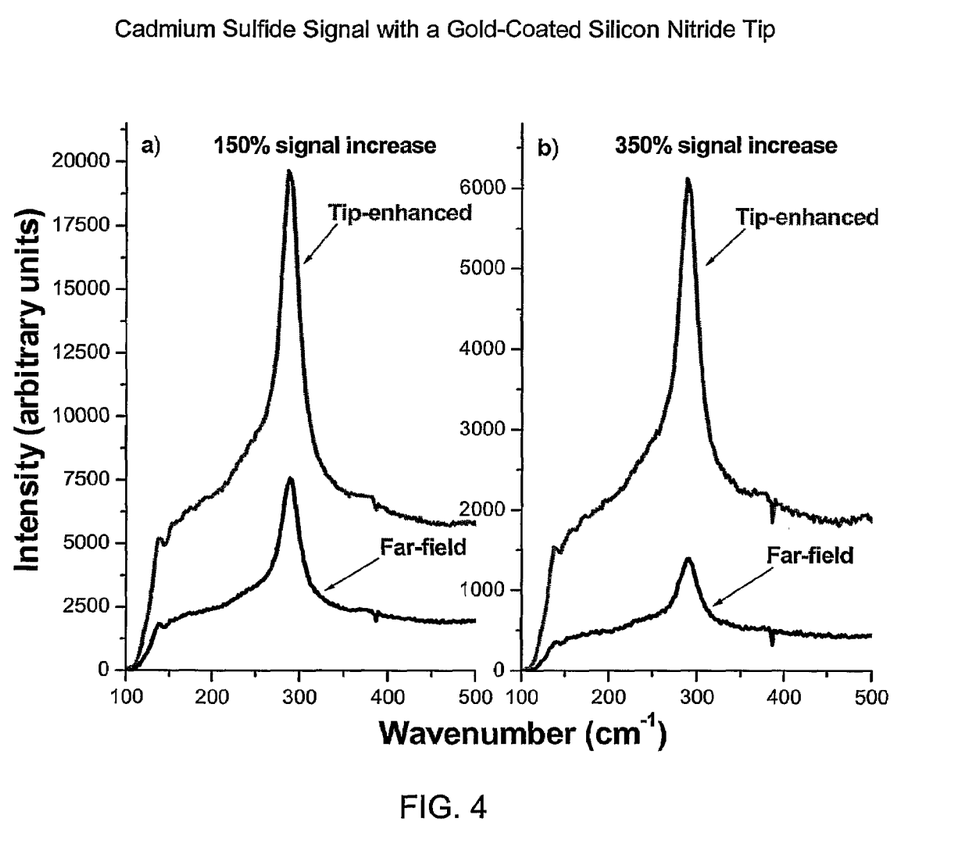
FIG. 4 provides a comparison of the tip-enhanced Raman signal contrast ratio obtained for CdS with conventional means (a) and the contrast ratio obtained according to the present invention (b)

FIGS. 4a and 4b are two graphs illustrating the occurrence of an increase in contrast due to the present invention. As can be seen when comparing FIG. 4a to 4b, the contrast of the CdS signal is increased 133% from the conventional polarization conditions of FIG. 4a (approximately 65°) to the polarization conditions of the present invention (FIG. 4b). In the case of CdS, the illumination polarization is, in one embodiment, about 55° to about 75° and the analyzed polarization is about 25°. In another embodiment, the analyzed polarization can be about 10° to about 40°, or even about 15° to about 35°.

Figure 5A:
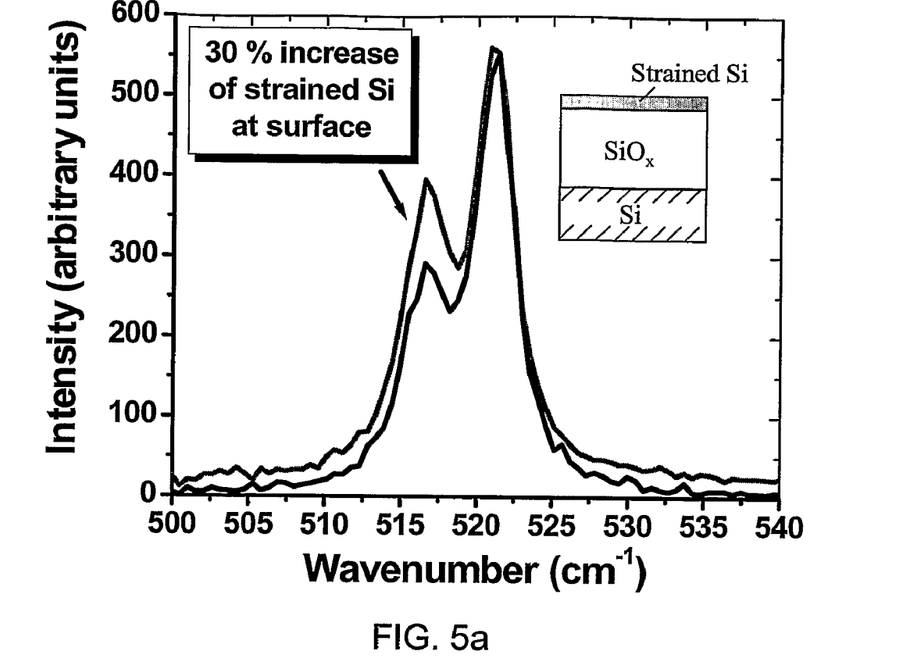
FIG. 5 shows in the inset a schematic cross-section of the strained silicon sample. The far-field Raman (black) and tip-enhanced Raman (gray) signals for strained Si and Si under conventional polarization conditions are shown in (a) and the corresponding Raman signals for polarization conditions under the present invention are shown in (b)
Figure 5B:
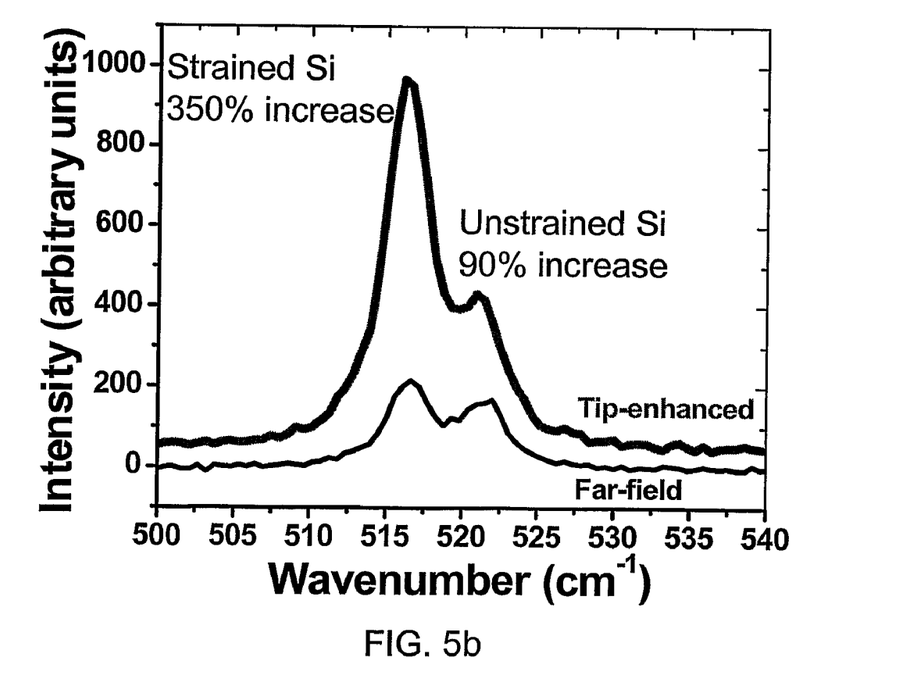

A demonstration of localization of the depolarized tip enhanced signal can be obtained on a multilayer structure that consists of a 30 nm strained Si layer on top of a 300 nm $SiO_x$ layer grown on a Si wafer (FIG. 5a—inset). Polarized measurements of the far-field signal using 514.5 nm laser light barely detect the contribution of the strained layer (FIG. 5a). Selection of a particular polarization geometry allows one to make the intensities of the far-field Raman signals from the strained and unstrained Si comparable (FIG. 5b). Bringing the apertureless tip in contact leads to enhancement of the Raman signal (FIG. 5b) from the strained silicon by approximately 350%, while an increase of only approximately 90% is observed for the signal from the unstrained silicon.

Figure 6:
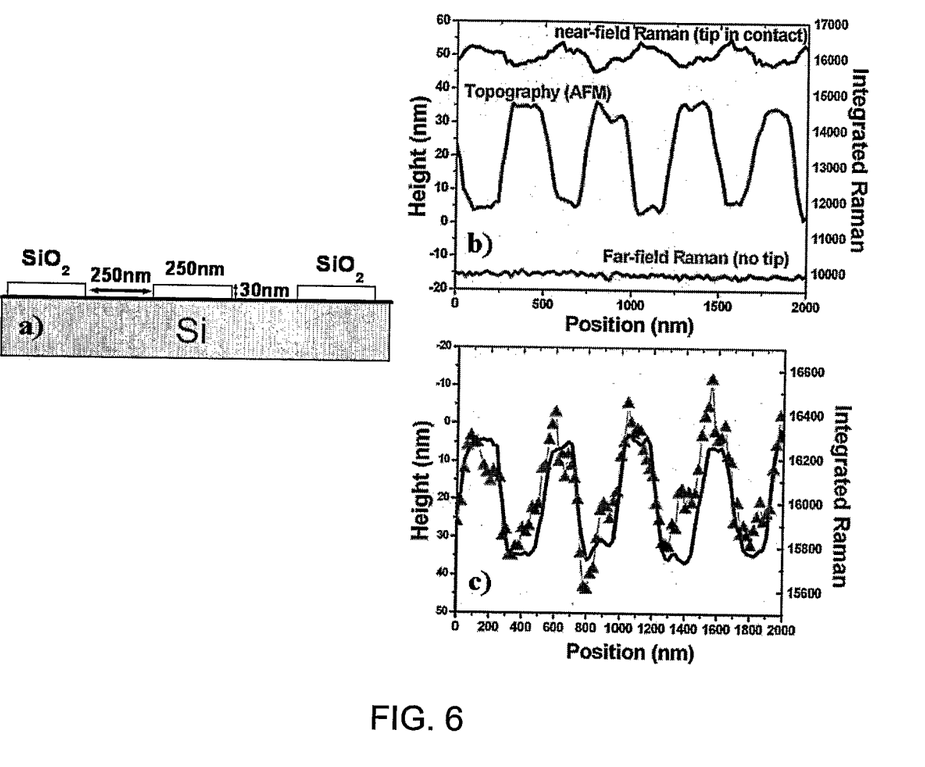
Figure 7:
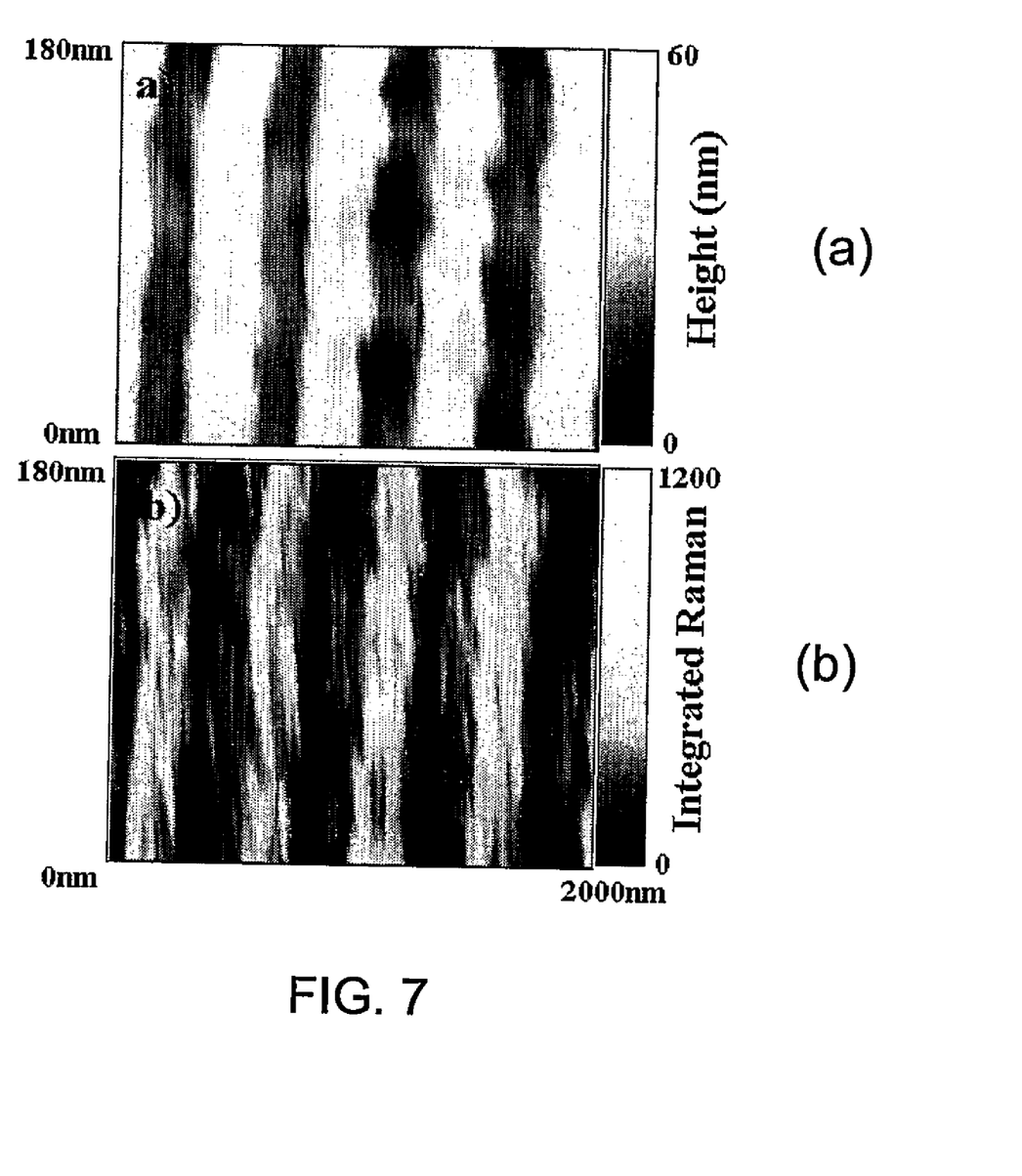

For the analysis of lateral resolution periodic $SiO_x$ structures are used on a Si wafer (FIG. 6a). Topographic and Raman signals are acquired simultaneously as the piezo-driven sample stage scanned in the XY plane with a step size of 20 nm. For this structure, the Raman signal from Si should be compared with the inverted topography. The near-field Raman signal follows well the inverted topography while no intensity modulation is visible in the far-field signal (see FIGS. 6b and 6c). Moreover, two-dimensional images also show excellent correlation between the topography of the sample (FIG. 7a) and the variation in the integrated Raman intensity of the Si mode (FIG. 7b).

Fits of the profiles (FIG. 6c) estimate an average full width at half maximum (FWHM) of 216±10 nm for the trench topography and 240±20 nm for the Raman signal. These results indicate extremely high lateral resolution, comparable to the scanning step size 20 nm. This analysis demonstrates that the use of the depolarized geometry provides sufficient contrast and localization of the enhanced signal for TERS of Si structures. The contrast as achieved on Si should be sufficient for practical applications, e.g., for analysis of stress distributions in Si structures at the nanoscale.

Figure 8:
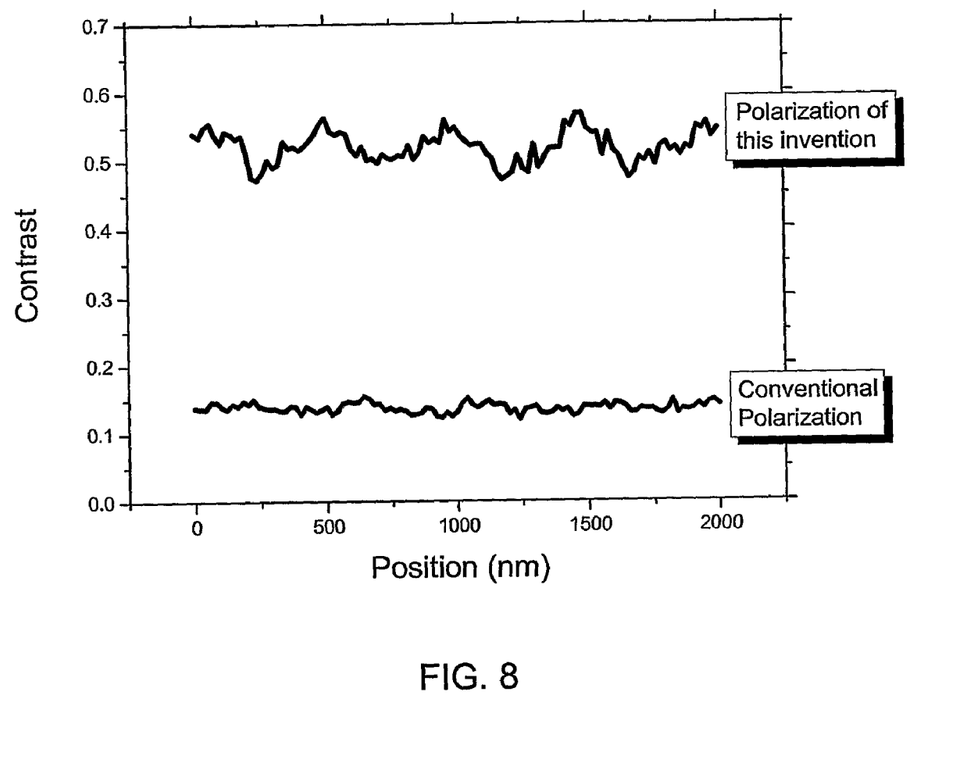
FIG. 8 is a graph illustrating a tip enhanced Raman line scan of an Si/SiO$_x$ structure formed in accordance with the design illustrated in FIG. 6a, showing increased contrast and resolution of the polarization scheme of the present invention when compared to a conventional polarization scheme.
Figure 9:
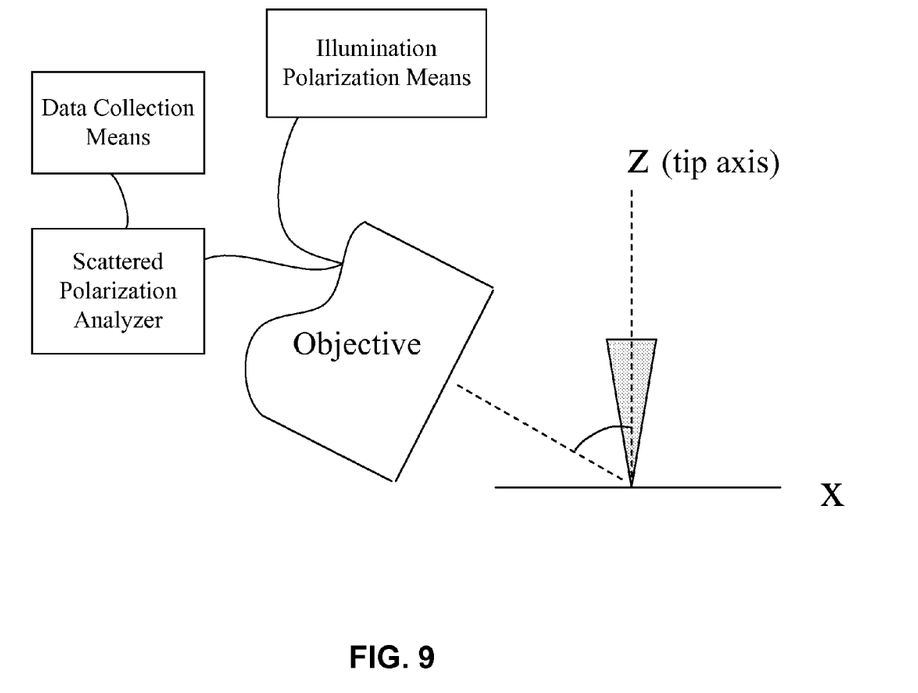
FIG. 9 is a schematic illustration of a metallic tip in contact with a specimen and details a illumination polarization means, a scattered light polarization analyzer, and a data collection means.

FIG. 8 shows the improvement of the present invention versus conventional polarization. The contrast for two line scans from the above mentioned $Si/SiO_x$ structures are shown in FIG. 8. The line scan using conventional polarization (nearly parallel to the tip, or from 0° to 25°) shows (i) a lower overall level of contrast between TERS and far-field scans (approximately 0.15); and (ii) less contrast variation along the line; it is almost featureless. The line scan obtained according to one embodiment of the present invention (optimum polarization and analyzer angles) resulted in (i) much higher overall contrast; and (ii) more pronounced contrast variation along the line. The improved resolution provided by the present invention, as demonstrated in FIG. 8, makes side-illumination tip-enhanced spectroscopy more applicable to nanoscale characterization of semiconductor materials.

The present invention is suitable for analyzing a variety of structures. Such structures include, but are not limited to, semiconductor structures, biological structures, polymer structures, or combinations thereof. In one embodiment, the present invention can be used to analyze a variety of semiconductor structures that include, but are not limited to, silicon wafers, cadmium sulfide films, periodic silicon structures, or combinations thereof.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method for conducting Raman spectroscopy, the method comprising the steps of:
    (a) using an illumination/collection optics objective to illuminate one or more samples with light, wherein the illumination/collection optics objective is oriented at an angle of about 10° to about 90° relative to the longitudinal axis of a tip;
    (b) using an illumination polarization means to polarize at least a portion of the light of step (a) thereby generating a polarization orientation in at least a portion of the light of step (a), wherein the polarization orientation is from about 50° to about 80° relative to the longitudinal axis of the tip;
    (c) using a scattered polarization analyzer to selectively transmit at least a portion of the polarized light from step (b), wherein the polarization of the light transmitted by the scattered polarization analyzer is oriented at an angle of about 0° to about 90° relative to the longitudinal axis of the tip so as to maximize the tip-enhanced Raman contrast and wherein the orientation angle of the scattered polarization analyzer is selected based on the nature of the one or more samples being analyzed; and
    (d) collecting spectral data generated in steps (a) through (c) via a suitable collection means for analysis.

2. The method of claim 1, wherein the orientation angle of the scattered polarization analyzer is from about 30° to about 90° relative to the longitudinal axis of the tip.

3. The method of claim 1, wherein the orientation angle of the scattered polarization analyzer is from about 40° to about 90° relative to the longitudinal axis of the tip.

4. The method of claim 1, wherein the orientation angle of the scattered polarization analyzer is from about 50° to about 80° relative to the longitudinal axis of the tip.

5. The method of claim 1, wherein the method is used to analyze one or more structures selected from semiconductor structures, biological structures, polymer structures, or combinations thereof.

6. The method of claim 5, wherein the method us used to analyze one or more semiconductor structures selected from silicon wafers, cadmium sulfide films, periodic silicon structures, or combinations thereof.

7. An instrument for conducting Raman spectroscopy comprising:
    (a) an illumination/collection optics objective lens designed to illuminate one or more samples with light, wherein the illumination/collection optics objective lens is oriented at an angle of about 10° to about 90° relative to the longitudinal axis of a tip;
    (b) an illumination polarization means designed to polarize at least a portion of the light of part (a) thereby generating a polarization orientation in at least a portion of the light of part (a), wherein the polarization orientation is from about 50° to about 80° relative to the longitudinal axis of the tip;
    (c) a scattered polarization analyzer designed to selectively transmit at least a portion of the polarized light from part (b), wherein the polarization of the light transmitted by the scattered polarization analyzer is oriented at an angle of about 0° to about 90° relative to the longitudinal axis of the tip so as to maximize the tip-enhanced Raman contrast and wherein the orientation angle of the scattered polarization analyzer is selected based on the nature of the one or more samples being analyzed; and
    (d) a data collection means designed to collect spectral data generated in parts (a) through (c) for analysis.

8. The instrument of claim 7, wherein the orientation angle of the scattered polarization analyzer is from about 30° to about 90° relative to the longitudinal axis of the tip.

9. The instrument of claim 7, wherein the orientation angle of the scattered polarization analyzer is from about 40° to about 90° relative to the longitudinal axis of the tip.

10. The instrument of claim 7, wherein the orientation angle of the scattered polarization analyzer is from about 50° to about 80° relative to the longitudinal axis of the tip.

11. The instrument of claim 7, wherein the instrument is used to analyze one or more structures selected from semiconductor structures, biological structures, polymer structures, or combinations thereof.

12. The instrument of claim 7, wherein the instrument is used to analyze one or more semiconductor structures selected from silicon wafers, cadmium sulfide films, periodic silicon structures, or combinations thereof.

* * * * *